(12) United States Patent
Roser

(10) Patent No.: US 6,602,222 B1
(45) Date of Patent: Aug. 5, 2003

(54) DISPOSABLE INJECTION DEVICE

(75) Inventor: Bruce Joseph Roser, Cambridge (GB)

(73) Assignee: Cambridge Biostability Ltd., Cambridge (GB)

( * ) Notice: Subject to any disclaimer, the term of this patent is extended or adjusted under 35 U.S.C. 154(b) by 74 days.

(21) Appl. No.: 09/689,640

(22) Filed: Oct. 13, 2000

(51) Int. Cl.⁷ ............................................. A61M 5/30
(52) U.S. Cl. ......................................... 604/68; 604/72
(58) Field of Search .................... 604/68, 218, 72; 128/207

(56) References Cited

U.S. PATENT DOCUMENTS

| | | | | |
|---|---|---|---|---|
| 2,704,542 A | | 3/1955 | Scherer | 128/173 |
| 3,057,349 A | | 10/1962 | Ismach | 128/173 |
| 4,266,541 A | | 5/1981 | Landau | 128/207 |
| 4,966,581 A | * | 10/1990 | Landau | 604/244 |
| 5,746,714 A | | 5/1998 | Salo et al. | 604/68 |
| 6,102,896 A | * | 8/2000 | Roser | 604/218 |
| 6,224,567 B1 | * | 5/2001 | Roser | 604/218 |

FOREIGN PATENT DOCUMENTS

| | | | | |
|---|---|---|---|---|
| EP | 0595508 | * | 4/1994 | A61M/5/30 |
| EP | 0595508 | | 5/1994 | |
| GB | 959397 | | 6/1964 | |
| WO | WO98/15307 | | 4/1998 | |
| WO | WO9815307 | * | 4/1998 | A61M/5/30 |
| WO | WO98/17332 | | 4/1998 | |

* cited by examiner

*Primary Examiner*—Henry Bennett
*Assistant Examiner*—Sabrina Dagostino
(74) *Attorney, Agent, or Firm*—Jacobson Holman PLLC

(57) ABSTRACT

The present invention is a hand-operated injector device for injecting parenteral medications consisting of a cap, a plunger, a base, and a snap means. The cap contains a hollow central finger which upon proper hand force, moves toward a narrow plunger with an ability to slide into an annular wide plunger within a self-contained injection capsule. The movement of the cap drives the narrow plunger toward a narrow injection orifice at the bottom the capsule containing liquid medicament through which, the medicament under high pressure, forms a liquid jet through subcutaneous tissue of the patient. The injector may contain an external spring assisted holder or an internal spring assisted holder where the central finger is modified so as to be spring loaded. Finally, the spring injector may contain a cocking tab and a reusable power case. The injector device requires little training to use, reduces pain, improves injection safety and eliminates the need for a check valve.

5 Claims, 16 Drawing Sheets

DISPOSABLE INJECTION DEVICE

BACKGROUND OF THE INVENTION

1. Field of the Invention

This invention relates generally to disposable injector devices and more specifically, a disposable injector device which does not require a check valve but rather, a self-contained injection capsule and spring aided delivery of medicament into subcutaneous tissue of a patient.

2. Description of the Prior Art

Vaccines and drugs in today's world, are effective in controlling disease; however, parenteral injections possess serious problems which have continued to persist since the first subcutaneous injection was performed in 1836 by Lafargue. [Aronson J K. Routes of Drug Administration: 7 Subcutaneous administration Prescriber's Journal 38 50–55 (1988).] For instance, the use of a standard hollow needle attached to a syringe is not only inherently dangerous and cumbersome, but requires thirteen different steps to be completed using accepted sterile techniques.

As early as the 1920s and 1930s, several incidents occurred involving the accidental injection of diesel fuel into the hands of engineers due to pinhole defects in high-pressure fuel lines. Fine streams of liquid under sufficient pressure behaved as a "liquid nail" and painlessly penetrated the skin. Since the 1940s, numerous designs for high-pressure liquid jet injectors loosely modeled after the principles of fuel injectors continued to be patented. However, most of the complex designs required precision engineering with dozens of machined parts, therefore, they are inherently expensive and complicated. To a large extent, the complexity was due to a perceived need to maintain high pressure throughout each injection as with the high-pressure fuel injectors. Scherer, on the other hand, realized in 1949 that high pressure was required only at the start of the injection in order to punch a hole or track through the tough epidermis. The remaining bulk of the injection could be subsequently infused along the track under much lower pressure. [Scherer U.S. Pat. No. 2,704,543 (1949)].

Standard high-pressure instruments, because of their complexity, were not considered disposable devices. Even though simplified designs do exist [Alchas et al EP Patent No. EP0595508 (1994)], such devices are still complex, expensive and not considered truly disposable. Instead, design improvements have mostly been directed toward production of robust and reliable heavy-duty machines capable of numerous injections at high rates for mass immunization campaigns. [Ismach U.S. Pat. No. 3,057,349 (1959), Landau U.S. Pat. No. 4,266,541 (1981), U.S. Pat. No. 5,746,714 (1988), D'Antonio et al PCT Patent No. WO98/17322 (1998), Parsons PCT Patent No. WO98/15307 (1988)]. Some of the aforementioned prior art, claim capability of 4,000 injections per hour.

Problems continued to threaten the status of jet injections when an outbreak of hepatitis B caused widespread concern in the vaccine industry. [Canter J; et al 1990. An outbreak of hepatitis B associated with jet injections in a weight reduction clinic. Arch. Intern. Med.; 150: 1923–7]. The transfer of the virus through jet injection and its mechanisms were explained at the World Health Organization (WHO) meetings. [J Lloyd. Status of Jet Injectors. SEE HYPERLINK (http://www.who.int/gpv-coldchain/Powerpoint Technet.htm and http://www.who.int/gpv-coldchain/Powerpoint Technet.htm)].

It appeared that high pressure occurring in the tissues, which were suddenly distended by the injection, coincided with falling pressure inside the jet injector. Ultimately, this caused a reflux flow or "sucking-back" of tissue fluid into the injector. Because of this serious drawback, single-use vials which insert into the mechanical injector were developed. [Parent du Châtelet el al Clinical immunogenicity and tolerance studies of liquid vaccines delivered by jet-injector and a new single-use cartridge (Imule): comparison with standard syringe injection. Imule Investigators Group. Vaccine, 15: 449–58 (1987)]. Cheap, plastic, replaceable nozzles and vaccine fluid paths for mechanical injectors have also been developed. Such injectors retain the multi-dose vial format as in Landau U.S. Pat. No. 4,966,581 (1990)].

A truly disposable liquid jet injector that operated on the new principle of using modest pressure of the human hand to generate a brief pulse of high pressure has been developed. This punches a narrow track through the skin to allow the subsequent delivery of the bulk of the dose at lower pressure. (Roser, B. Disposable Injector Device U.S. Pat. No. 6,102,896). However, these designs still suffer from several disadvantages. The power derived from steady pressure of the hand, converts to a sharp pulse of high-pressure following the structural failure of "snap tabs" or the sudden overcoming of the resistance of "snap rings." The liquid dose to be injected is located in a centrally located reservoir, and the high pressure barrel is located in the base of the injector itself which also has an injection orifice in the base. Such an invention, places demands on manufacture and assembly. Both the liquid reservoir assembly and the injector itself need sterile manufacture; engineering to withstand high pressure pulses; and a valve system to isolate the high pressure pulse from the hand activating the device. This leads to an increase in production costs.

Additionally, the completion of the power stroke is dependent upon the maintenance of hand pressure until the full dose of liquid is delivered. This leaves room for error, namely, it cannot be guaranteed that a reflex arrest of hand pressure could not occur under unusual circumstances, aborting the injection before the designed dose is delivered. A preferred solution to these problems is a self-contained injection capsule which can be driven to complete the power stroke by stored energy, thereby eliminating the need for check valves.

SUMMARY OF THE INVENTION

The present invention addresses the aforementioned drawbacks, and it is also cheaper to manufacture and assemble. Furthermore, it is possible to separate the dose capsule and the power assembly, meaning injection kits could contain a single power device and multiple dose capsules. Although superficially similar to the Imule concept [Parent du Châtelet et al Clinical immunogenecity and tolerance studies of liquid vaccines delivered by jet-injector and a new single-use cartridge (Imule): comparison with standard syringe injection. Imule Investigators Group. Vaccine, 15: 449–58 (1997)], the design of the separate injection capsule in the present invention is novel and far superior.

Central to this improvement is a narrow-bore element of a plunger design, which forces a small volume of a dose under high-pressure through the skin to provide an injection track, which element forms a part of the low-pressure plunger which subsequently delivers the bulk of the dose. In addition, a fine injection orifice is incorporated into the other end of the injection capsule thereby making the entire liquid path fully self-contained. Essentially, the plunger is a two-component telescopic assembly in which a narrow plunger is centrally located concentrically in a wider plunger of annular shape. The "orifice end" of the narrow plunger tightly fits in a cylindrical cavity which formed in the central portion of the annular wide plunger. The major portion of the narrow plunger is located further from the injection orifice than the annular wide plunger, thus defining a volume of liquid in the central portions of the annular wide plunger which generates a high-pressure jet during the injection stroke.

To address the problem of lack of guaranteed completion of the power stroke, one solution is to transiently store the energy generated by hand pressure in a spring and releasing the stored energy by means of a snap device. By tensioning the spring only at the time of use, the power stroke is in minimal danger of prematurely aborting the injection. This avoids the need for storage of energy in the device while on the shelf, since doing so can lead to degradation of the material and stored energy over time, thereby reducing the shelf-life of the device.

A spring which is not under tension while stored, whether a conventional metal spring or gas spring, does not undergo material fatigue or energy leakage. Rather, maximum potential energy conferred by hand is delivered as a kinetic force, at the time of use.

BRIEF DESCRIPTION OF THE DRAWINGS

Several embodiments of the invention are illustrated and described in the accompanying drawings, forming a part of the specification, wherein.

DETAILED DESCRIPTION OF THE PREFERRED EMBODIMENTS

Figure 1:
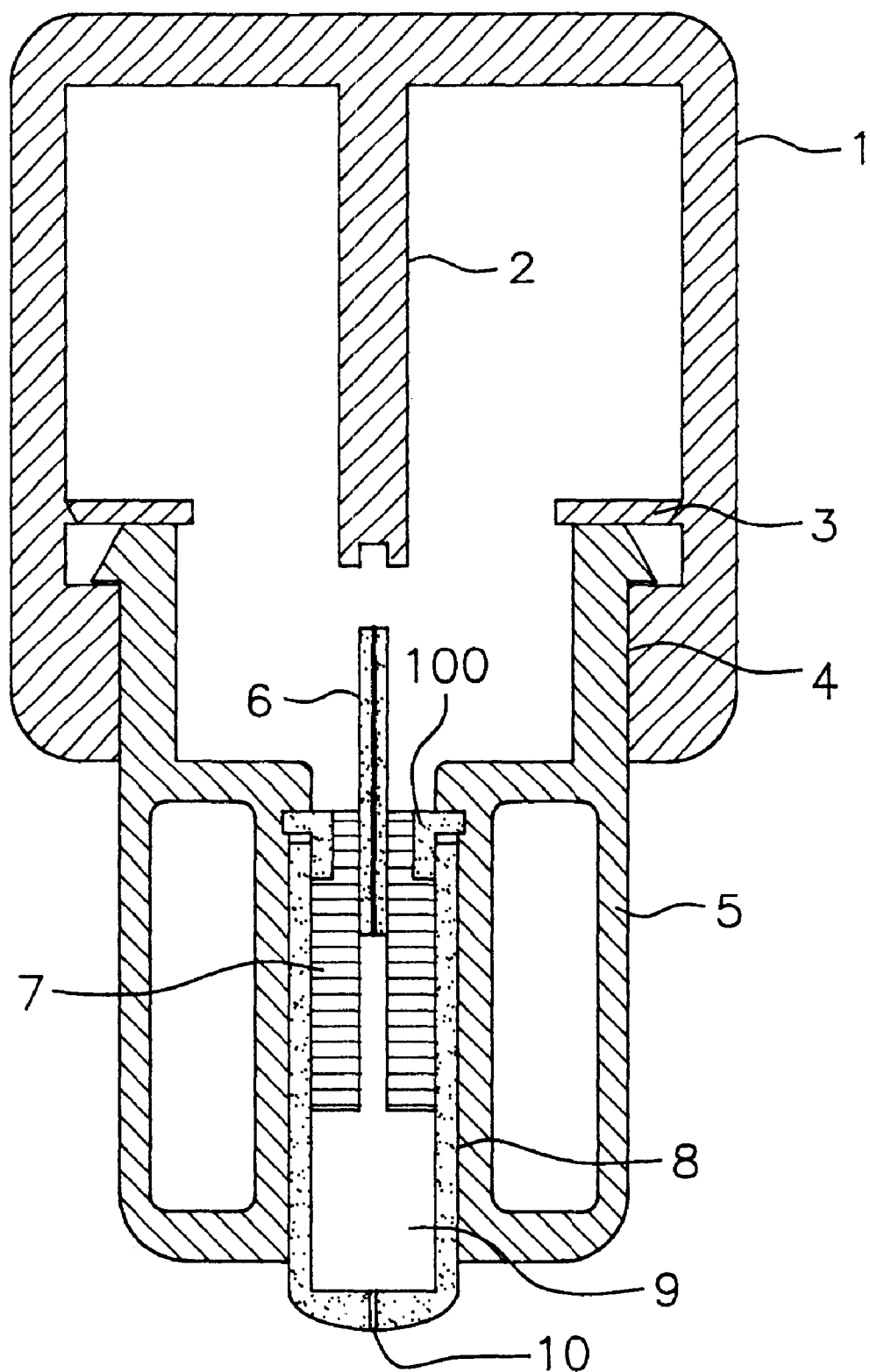
FIG. 1 is a cross-sectional view of a tabjet injector device, the device consisting essentially of two parts: a power case having a cap and central finger, and contained within the power case is an injection capsule consisting of a narrow plunger centrally located within a wide annular plunger fitted in a dosage capsule containing medicament to be injected.

As can be seen in FIG. 1, a tabjet injector device consists of a power case having a cap 1 and a central finger 2. The cap 1 is movable on a base 5 but is prevented from movement by break tabs 3. The base 5 contains an injection capsule made up of a narrow plunger 6, a wide annular plunger 7, a dosage capsule 8, a narrow injection orifice 10 and an integral collar, 100 on the end of the dosage capsule 8 opposite from the injection orifice 10. The narrow plunger 6 is movable in a centrally located cylindrical space within the wide annular plunger 7. The narrow plunger 6 as well as the wide annular plunger 7 create a composite plunger situated in the dosage capsule 8. The dosage capsule 8, containing medicament 9 to be injected, has the narrow injection orifice 10 at the bottom end.

Figure 2A:
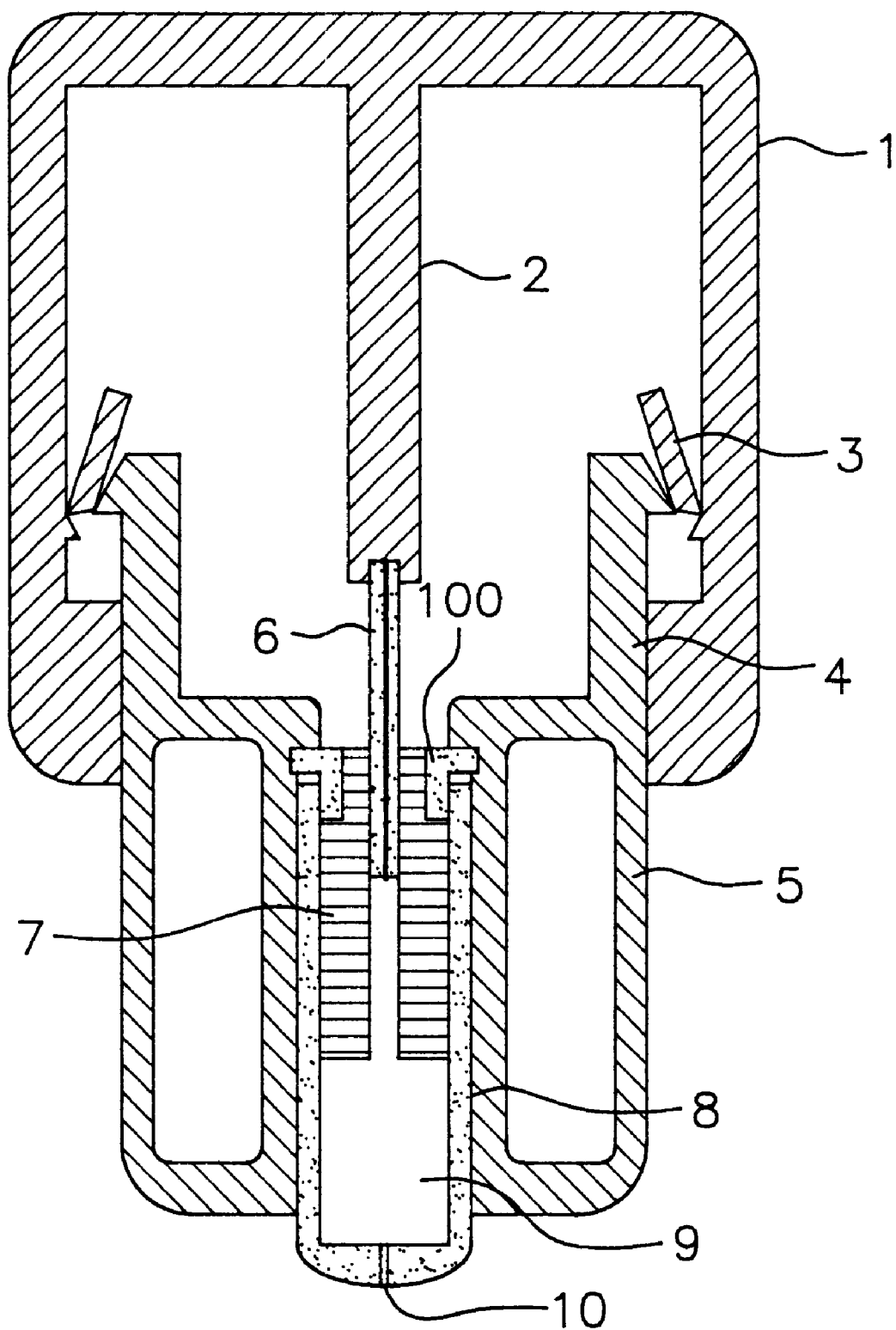
FIGS. 2A–C are cross-sectional views of the tabjet injector device, showing in succession, the break tabs yielding and allowing the central finger of the cap to strike the narrow plunger; the continued pressure driving the narrow plunger through the wide annular plunger until the central finger of the cap strikes the top of the wide annular plunger thereby punching a track through the epidermis; and finally, the central finger of the cap driving the composite narrow and wide plungers toward the orifice to deliver the bulk of the medicament through the injection track.
Figure 2B:
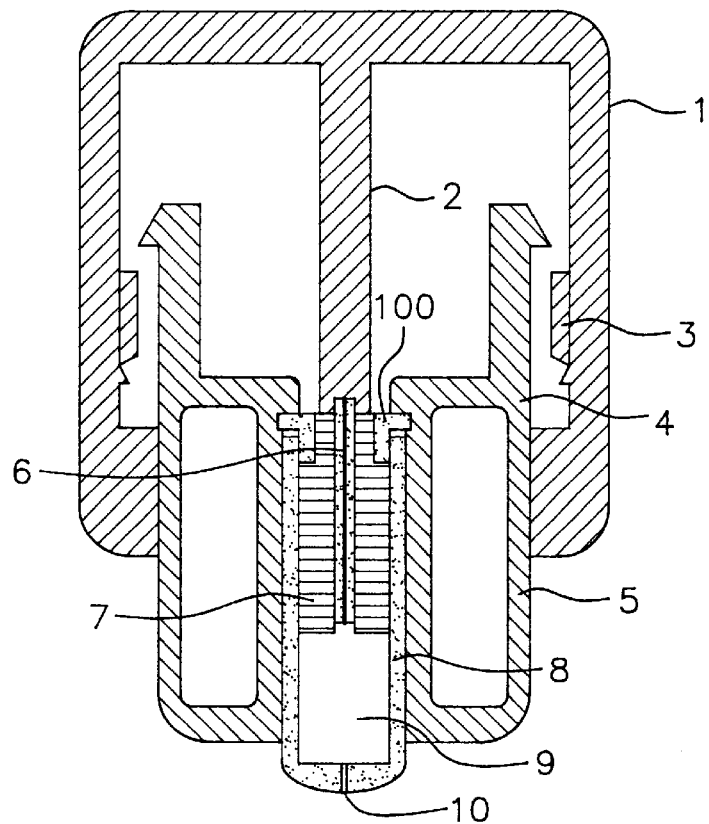
Figure 2C:
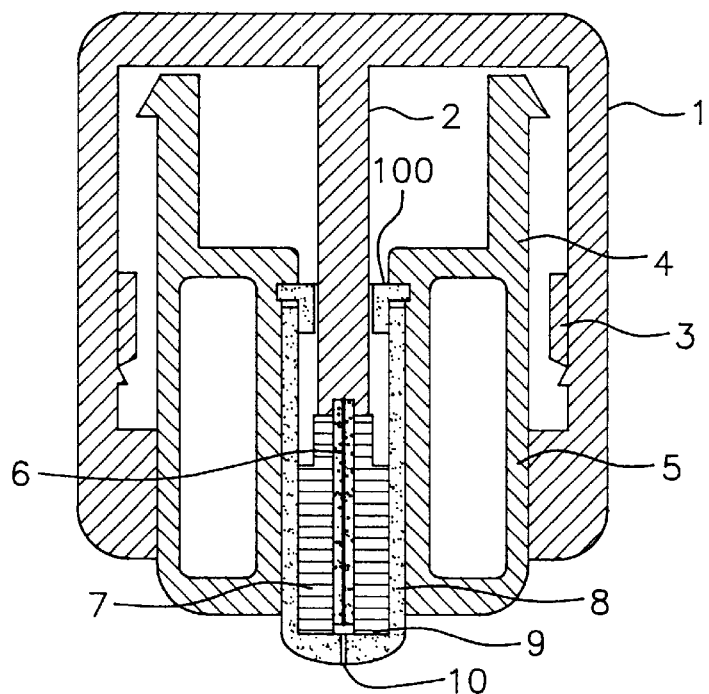

Three distinct stages of operating the tabjet injector device are identified in FIGS. 2A–C. In FIG. 2A, when sufficient force is exerted on the cap 1, the break tabs 3 yield allowing the central finger 2 of the cap 1 to strike the narrow plunger 6. Continued pressure drives the narrow plunger 6, as seen in FIG. 2B, through a cylindrical hole in the wide annular plunger 7 forming a single composite plunger. When the central finger 2 of the cap 1 strikes the top of the narrow plunger 6, there is a tendency for this pressure to push the annular wide plunger 7 backward out of the dosage capsule 8. This is prevented by an integral collar 100 on the end of the dosage capsule 8. This high pressure pulse phase of the power stroke shoots a narrow stream of liquid through the narrow injection orifice 10 punching a track through the epidermis of a patient. Finally, in FIG. 2C, the central finger 2 of the cap 1 drives the composite plunger toward an orifice 10 to deliver the bulk of the medicament through the injection track previously punched through the epidermis. Because of this simple mechanism, the need for check valves, which confine the high pressure pulse, is eliminated, as a result greatly simplifying construction, increasing reliability and reducing costs.

Figure 3:
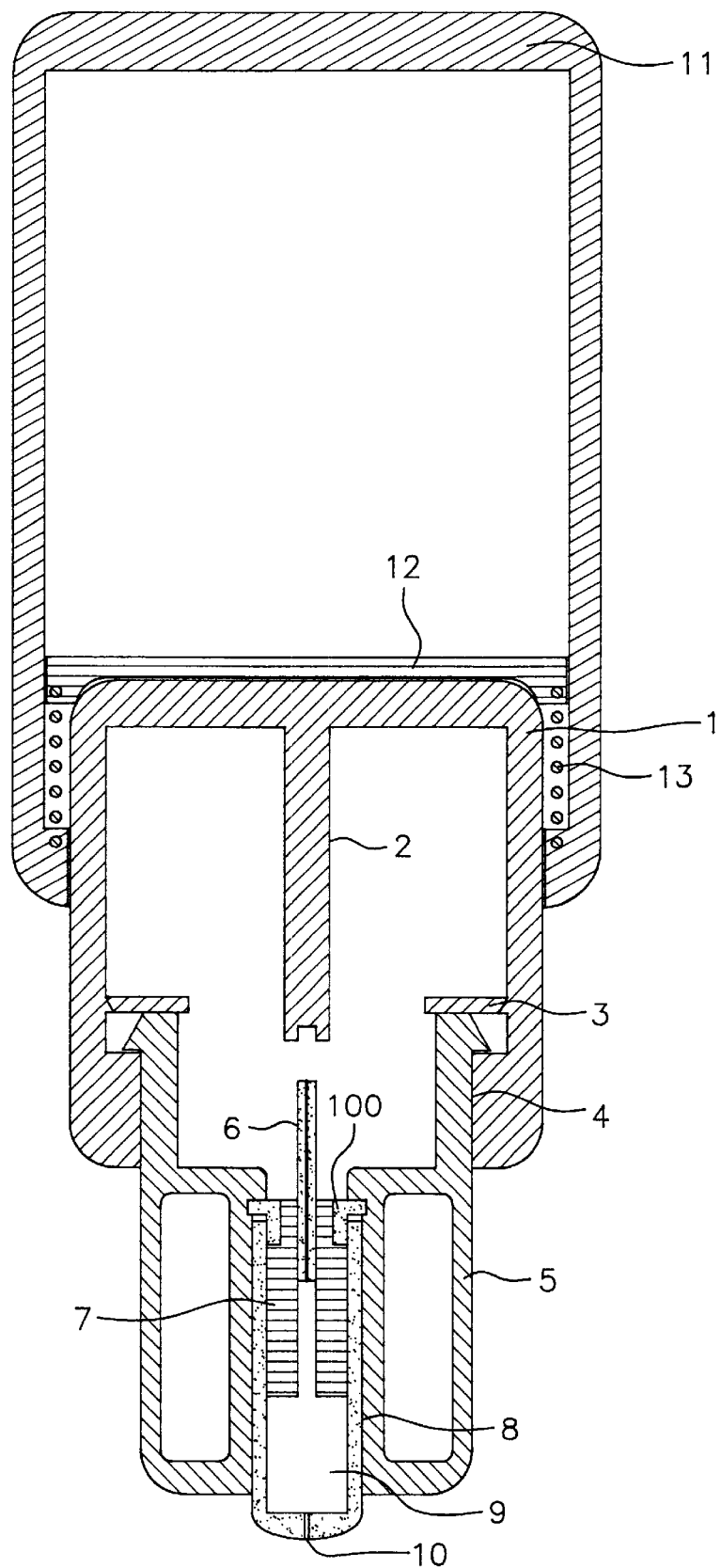
FIG. 3 is a cross-sectional view of a second embodiment of the tabjet injector device wherein a spring assisted holder having a cap containing a freely moveable partition and attached by means of a coil spring to the holder assists in moving the cap and central finger.

FIG. 3 depicts an external spring injector where the device of FIG. 1 is located inside a spring assisted holder consisting of a cap 11 containing a freely moveable partition 12 attached to it by means of a coil spring 13.

Figure 4A:
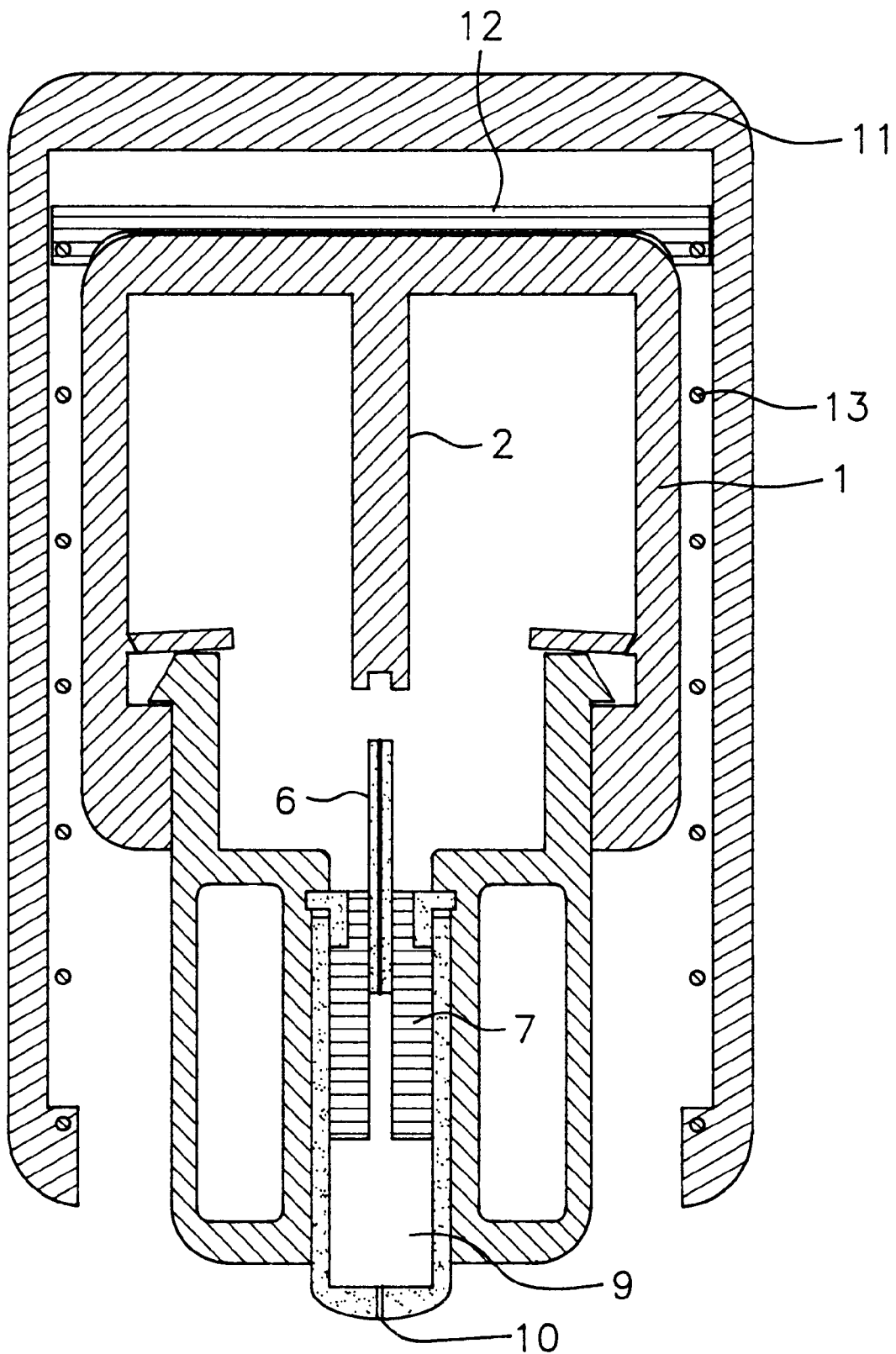
FIGS. 4A–D are cross-sectional views of FIG. 3, showing in succession: the spring assisted holder moving toward the patient's skin thereby, tensioning the coil spring until the break tabs yield; and finally, the power stored in the tensioned coil spring causing the freely mobile partition to complete the power stroke.
Figure 4B:
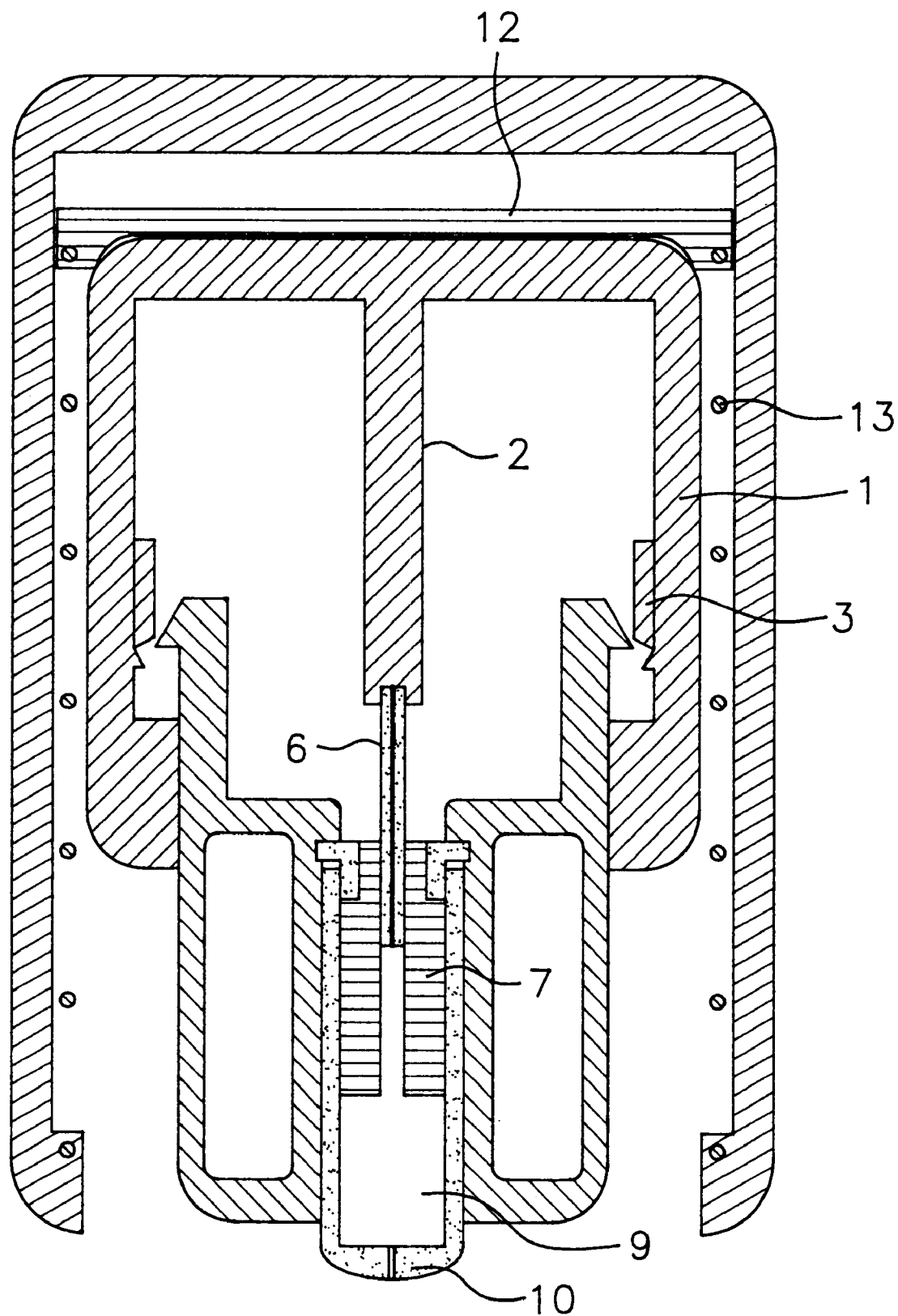
Figure 4C:
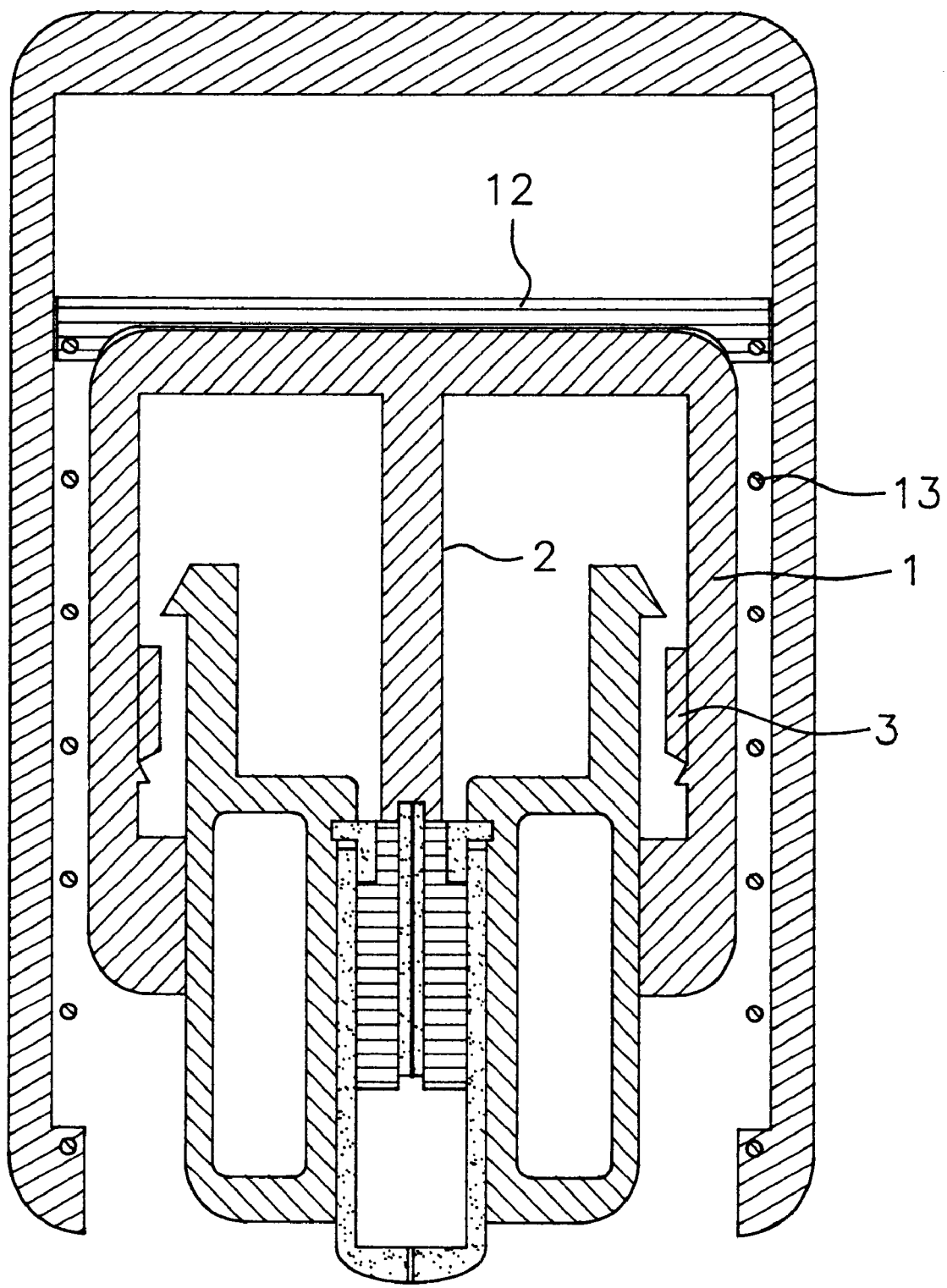
Figure 4D:
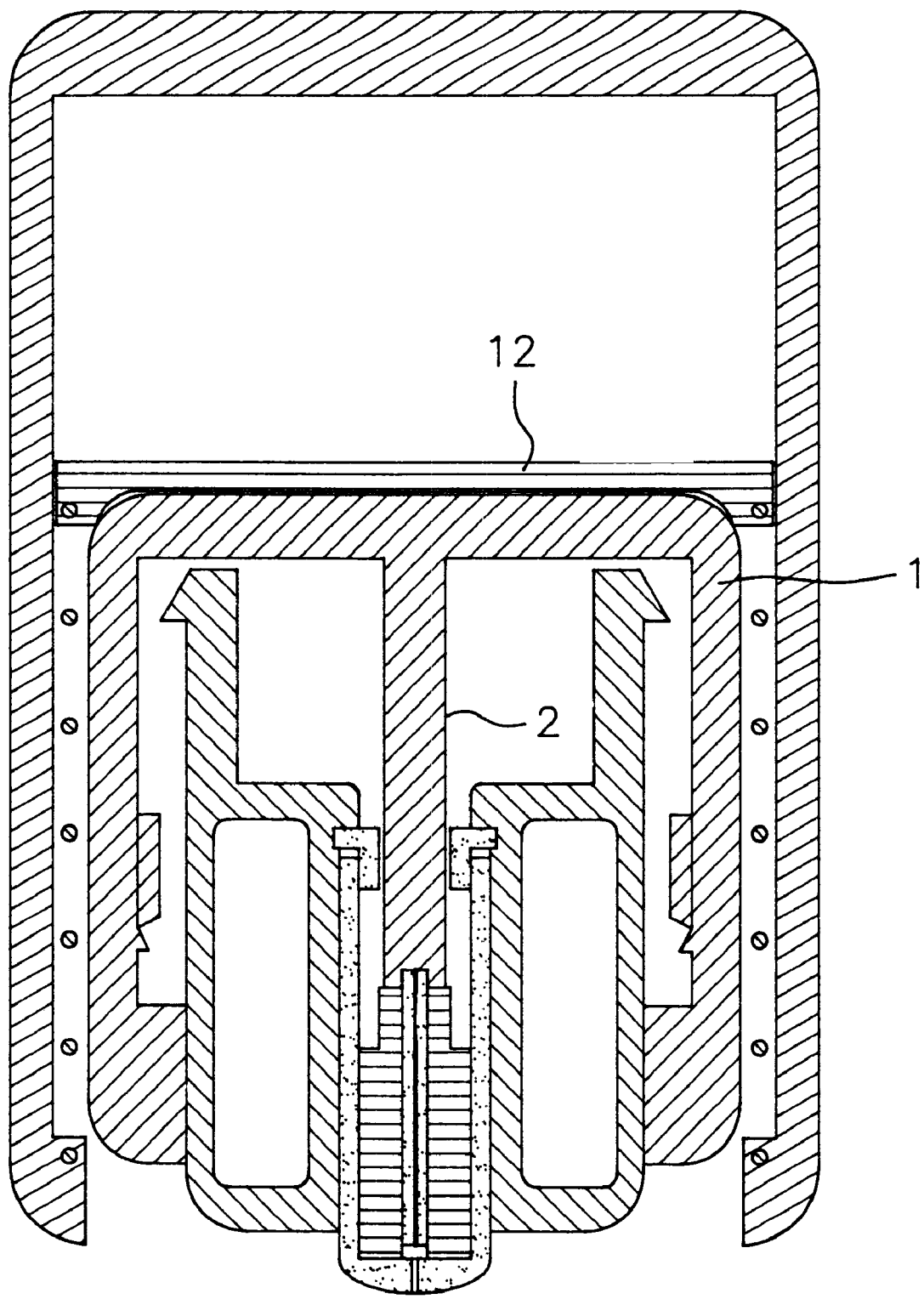

As seen in FIGS. 4A–D, in order to operate the external spring injector, hand pressure on the cap 11 of the spring assisted holder drives the cap 11 toward the patient's skin. An integral coil spring 13 is tensioned by the hand force on the cap 11 of the spring assisted holder as it slides over the injector and is arrested by contact with the patient's skin. (FIG. 4A.) At this point, the pressure exerted on the cap 11 of the injector device via the freely movable partition 12 and the coil spring 13 is sufficient to snap the break tabs 3. This causes the central finger 2 of the cap 1 to strike the narrow internal plunger 6 leading to a sharp rise in pressure in the fluid reservoir and the onset of the high pressure injection pulse (FIG. 4B) and the continuing pressure caused by the coil spring 13 then drives the narrow plunger 6 through the wide annular plunger 7 to complete the high pressure injection pulse which terminates when the central finger 2 of the cap 1 strikes the wide annular plunger 7, see FIG. 7C. Continuing tension on the coil spring 13 in the spring assisted holder drives the composite plunger to the end of the injection capsule thereby delivering the complete medicament dosage, see FIG. 4D.

The spring device may also be a gas spring which is easily achieved by making a seal between the moveable partition 12 in the spring assisted holder and the cap 11. The volume of air inside the spring assisted holder acts as an energy store eventually achieving complete injection in a similar manner to the coil spring 13 as seen in FIGS. 3 and 4.

Figure 5:
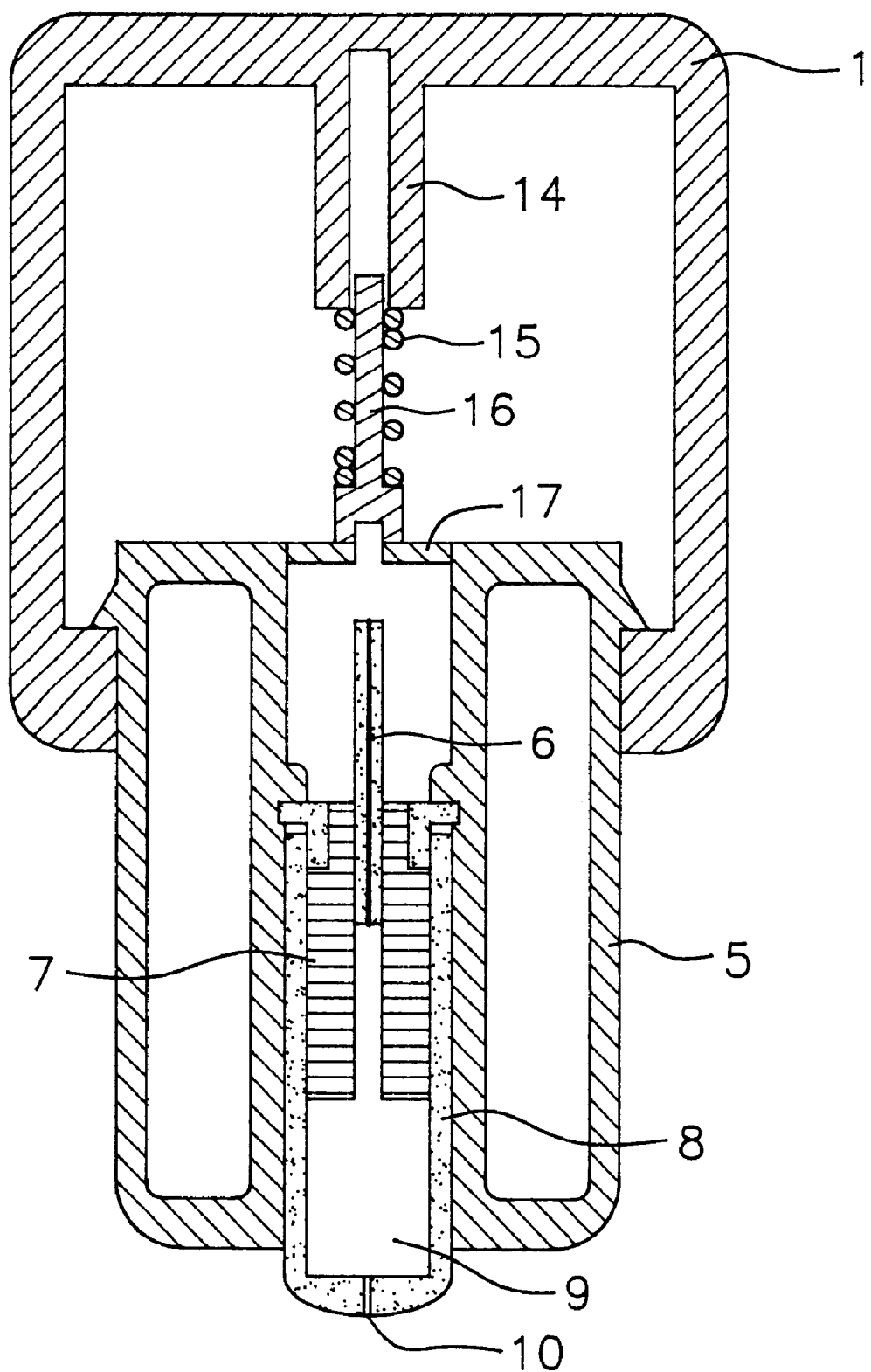
FIG. 5 is a cross-sectional view of a third embodiment of the tabjet injector device modified so the central finger is hollow containing a freely movable member, there being a coil spring surrounding the freely movable member.

The device in FIG. 5, an internal spring injector, has a modified central finger 14 attached to the cap 1 in order to be spring loaded. The central finger 14 is hollow and contains a freely movable member 16. Between the hollow central finger 14 and the movable member 16, is a coil spring 15. The freely movable member 16 is prevented from moving toward the orifice 10 by centrally located break tabs 17 relocated to the space above the narrow plunger 6.

The coil spring 13 (in tension) of FIG. 3 and/or the coil spring 15 (in compression) of FIG. 5 can be replaced with an elastomeric spring. The elastomer can either be synthetic or natural rubber, synthetic being preferred because of the perishability problems with natural rubber.

Figure 6A:
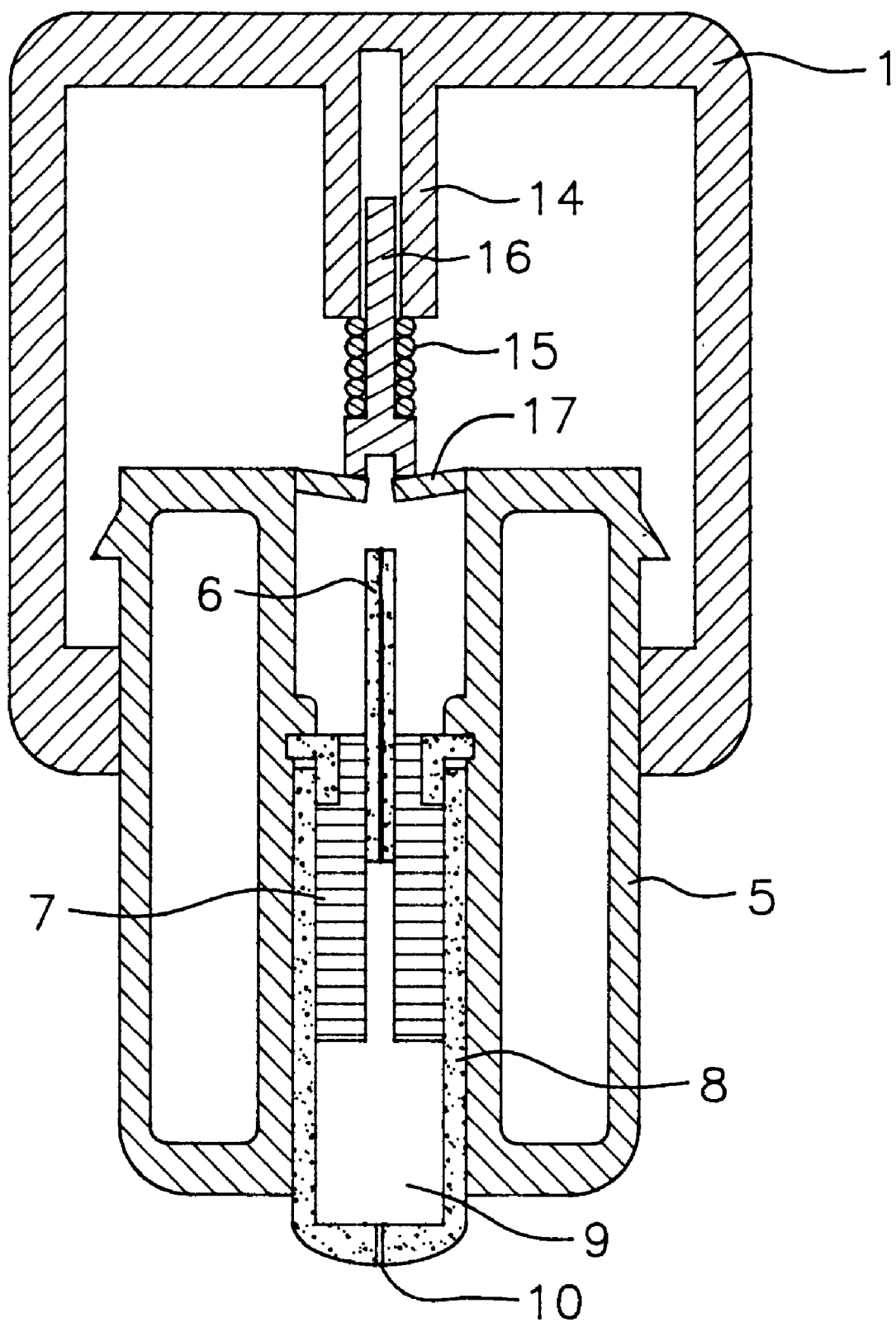
FIGS. 6A–D are cross-sectional views of FIG. 5, showing in succession: compression of the coil spring; the break tabs yielding; and the power stored in the coil spring causing the power stroke to go to completion.
Figure 6B:
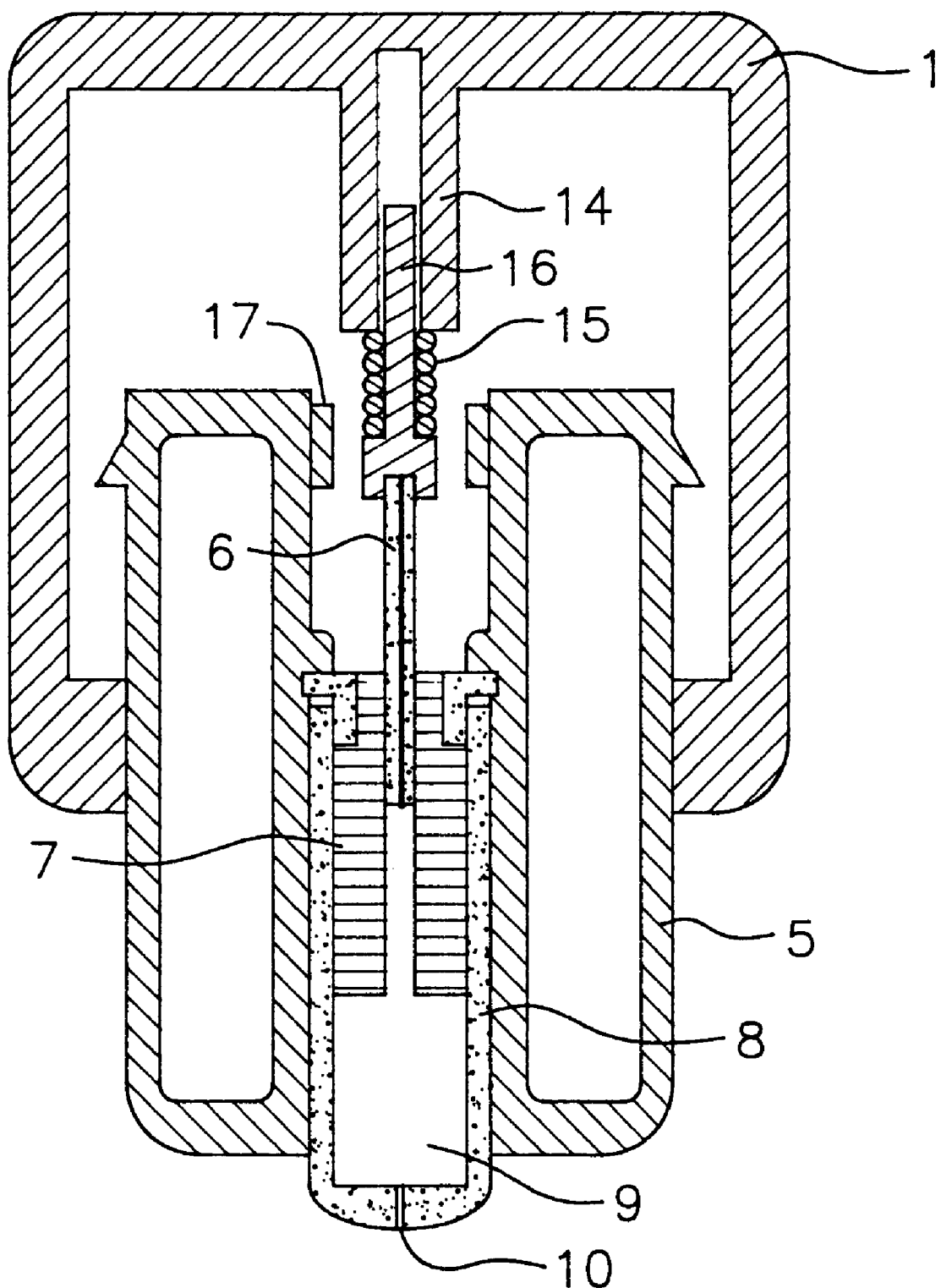
Figure 6C:
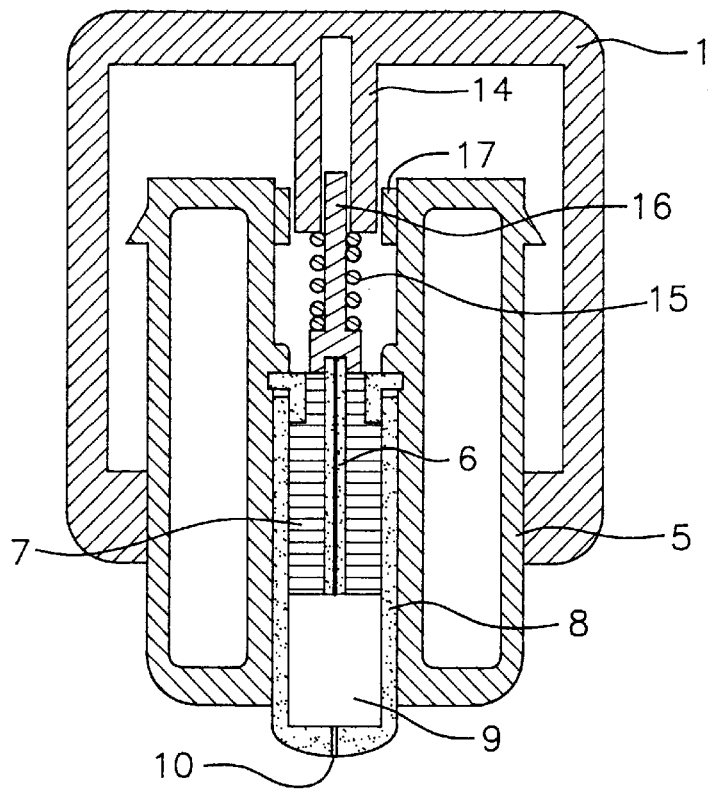
Figure 6D:
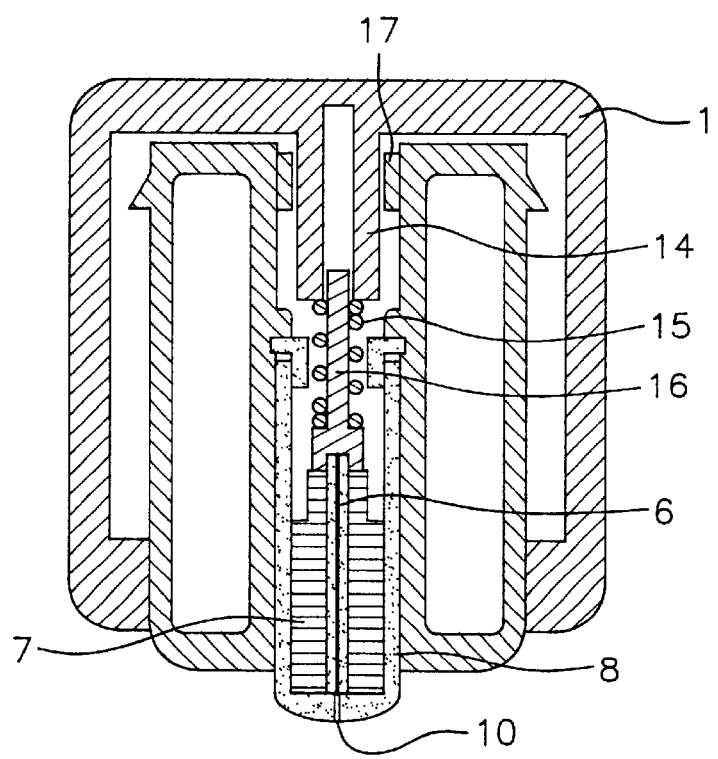

FIGS. 6A–D depict the operation of the internal spring injector. In this embodiment, tension is stored in the spring during the initial movement of the cap 1 of the injector which diverts force away from the break tabs 17 until the spring is fully compressed. At this point, hand pressure conveys directly to the break tabs 17 which ultimately give way. A combination of the release of energy stored in the coil spring 13 and the continued cap movement accomplish the injection. In FIG. 6A, when sufficient force is exerted on the cap 1, the spring 15 is compressed and the break tabs 17 yield. As seen in FIG. 6B, the break tabs 17 completely yield allowing the movable member 16 to hit the top of the narrow plunger 6. The narrow plunger 6 moves through the wide annular plunger 7, see FIG. 6C, punching a track through the epidermis until the bottom end of the movable member 16 reaches the top of the wide annular plunger 7 forming a composite plunger. This composite plunger then continues its downward movement discharging the medicament 9 through the orifice 10 by the force of coil spring 15, see FIG. 6D.

Figure 7:
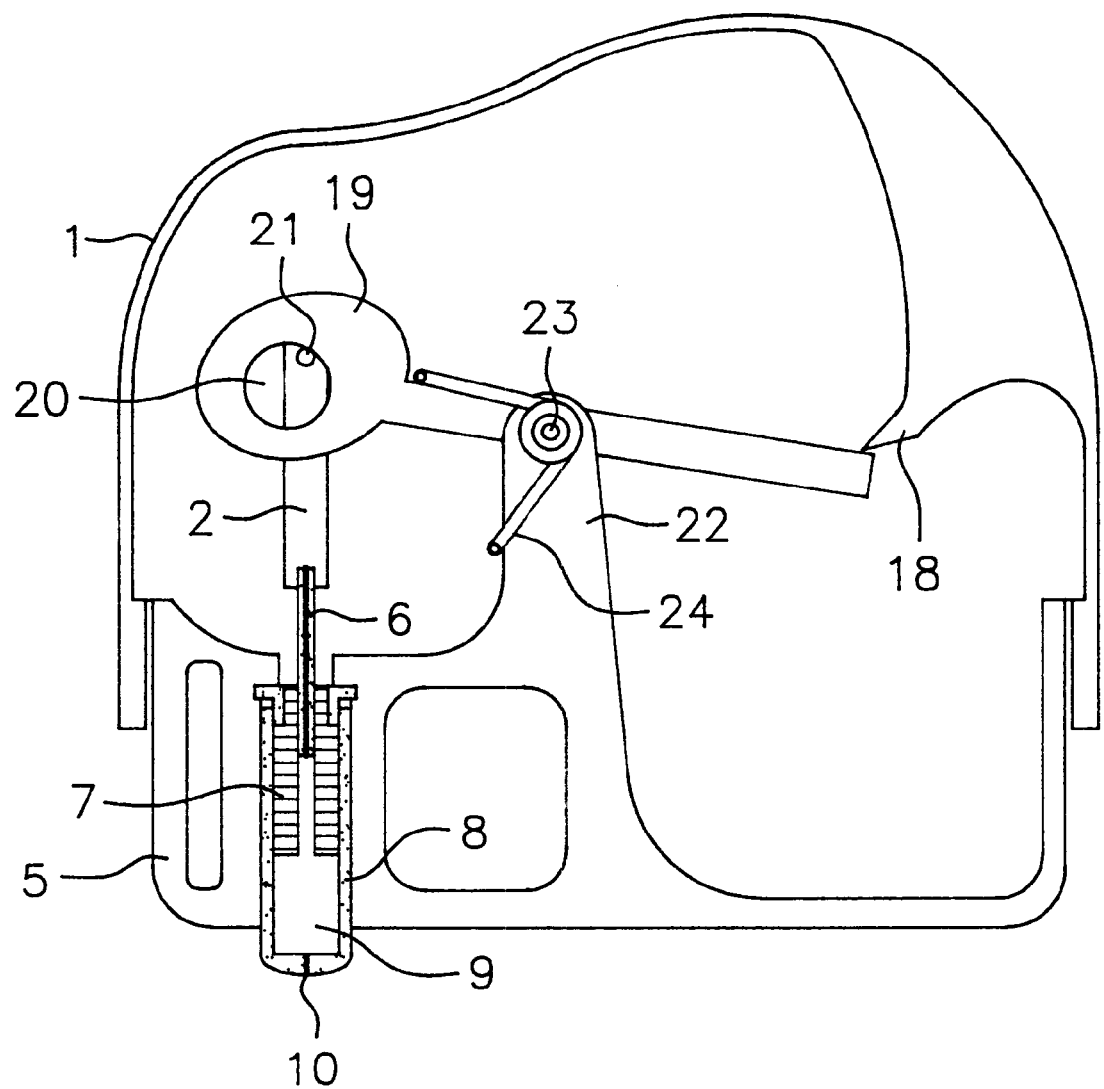
FIG. 7 is a cross-sectional view of a fourth embodiment which is a cocked spring injector device consisting of a cocking tab which presses on a rocking lever having a driving hole; the rocking lever rotates about a fulcrum and the central finger transmits force to a narrow plunger of the injection capsule.

A cocked spring injector device is seen in FIG. 7 and carries the additional advantage of being reusable. It has a cap 1 and integral with the cap 1 is a cocking tab 18 which presses on a rocking lever 19 with a weighted bulbous end having a driving hole 20 and a free or opposite end on which the cocking tab 18 acts. The rocking lever 19 rotates about a fulcrum 23 creating tension in a spiral spring 24 held in place against a post 22 through which the fulcrum 23 passes.

Figure 8A:
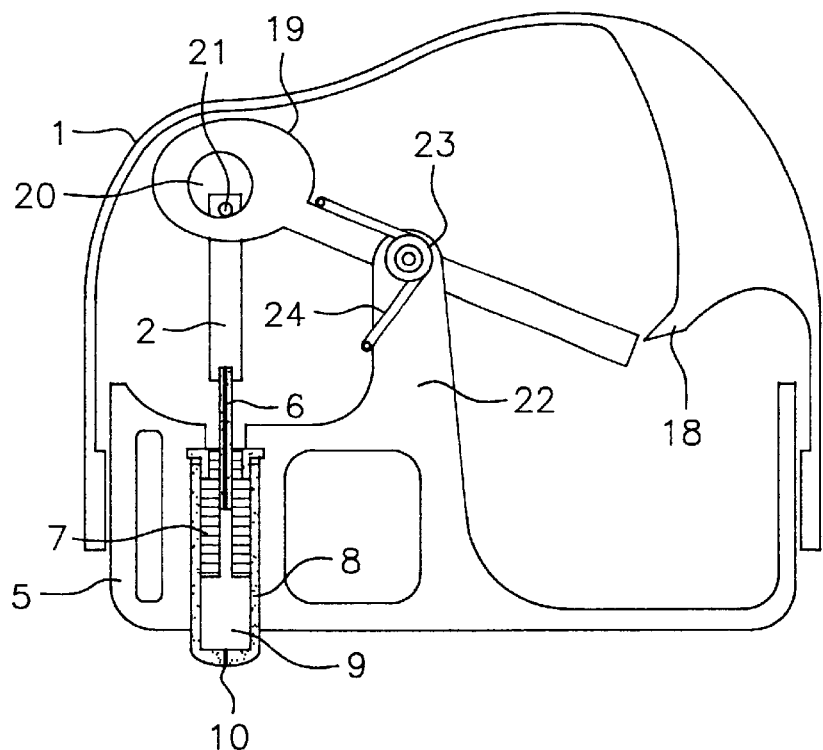
FIGS. 8A–D are cross-sectional views of a FIG. 7 showing in succession: the cocking tab pressing on the rocking lever thereby rotating it about the fulcrum until the cocking tab slips off the rocking lever, the released rocking lever snaps back in the opposite direction causing the rocking lever to push the narrow plunger, which then slides through the wide annular plunger punching a track through the epidermis and forming a composite plunger which finally drives toward the orifice end of the injection capsule to deliver the bulk of the medicament.

The central finger 2 is at the distal end of the rocking lever 19 and has a transverse rod 21 located in the driving hole 20 which carries the weight of the central finger 2 and the narrow plunger 6 of the injection capsule, see FIG. 8A.

Figure 8B:
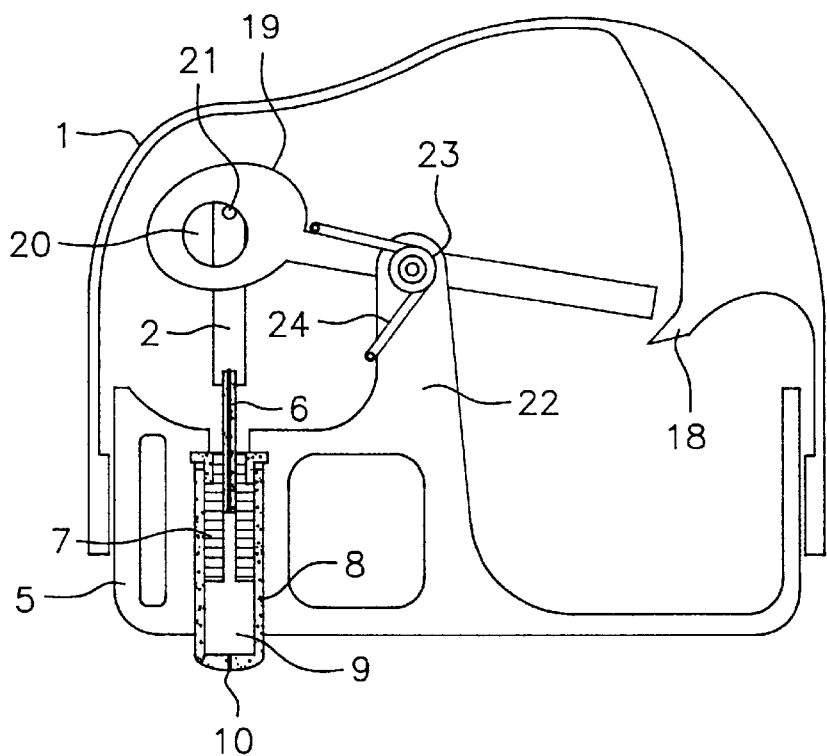
Figure 8C:
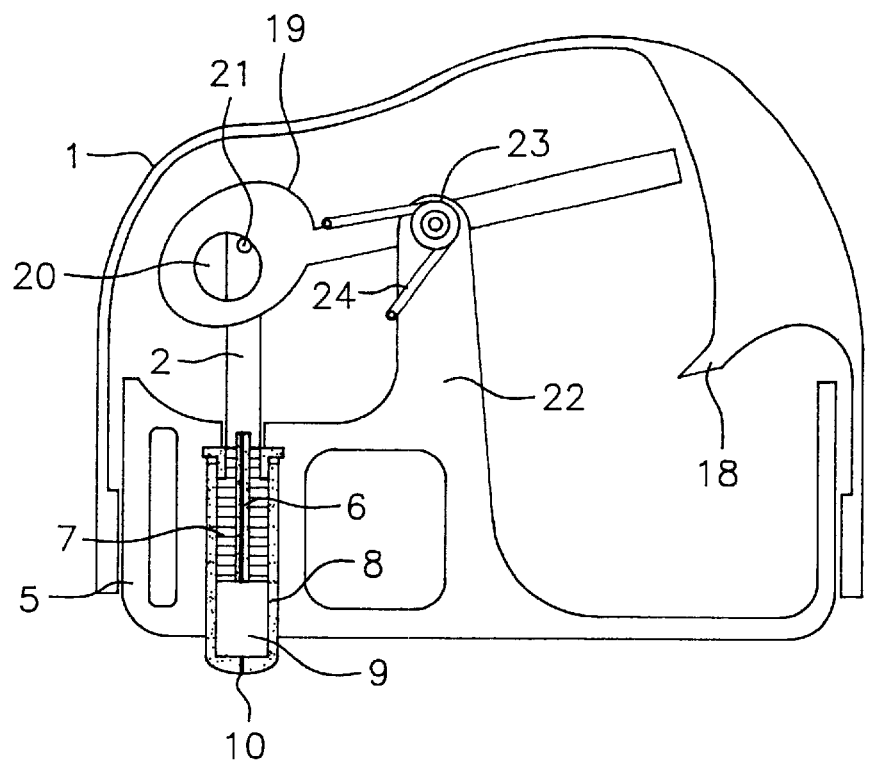
Figure 8D:
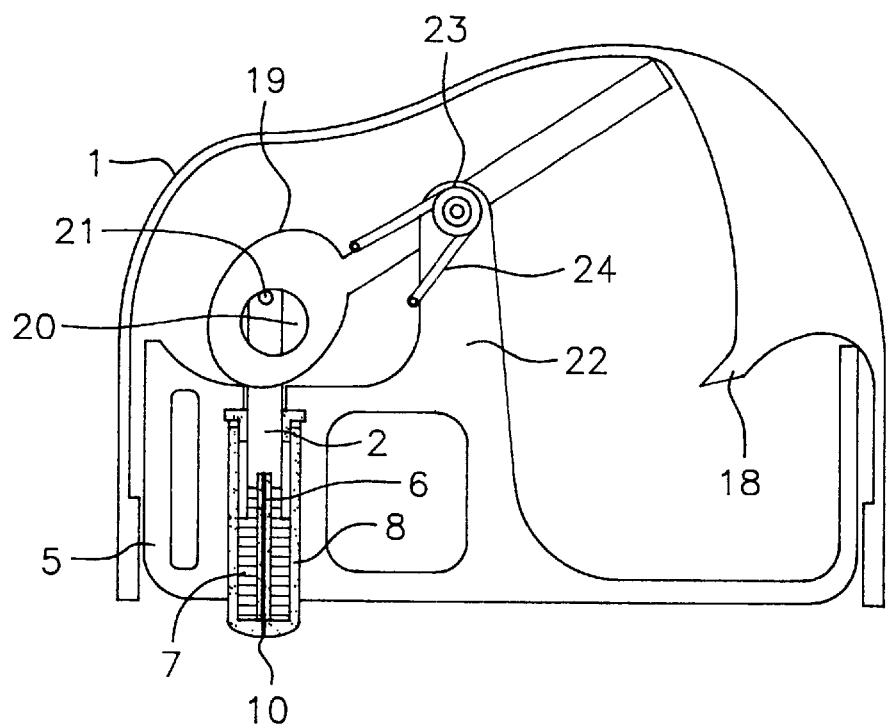

In operating the cocked spring injector, downward pressure is exerted on the cap 1, which causes the cocking tab 18 to press downward on the free end of the rocking lever 19. This ultimately causes the rocking lever 19 to rotate about the fulcrum 23 which creates tension in the spring 24 until the cocking tab 18 slips off the free end of the rocking lever 19, see FIG. 8A. The released rocking lever 19 snaps backward in the direction opposite to its rotation about the fulcrum 23 which causes the weighted end of the rocking lever 19 to push the narrow plunger 6 via central finger 2 and transverse rod 21, see FIG. 8B. Continued tension in the spiral spring 24 forces the narrow plunger 6 to move through the wide annular plunger 7, see FIG. 8C, forming a composite plunger and punching a track through the epidermis. Finally the composite plunger is driven toward the orifice 10 of the injection capsule by spring tension delivering the bulk of the medicament 9 from the dosage capsule 8, see FIG. 8D.

Figure 9:
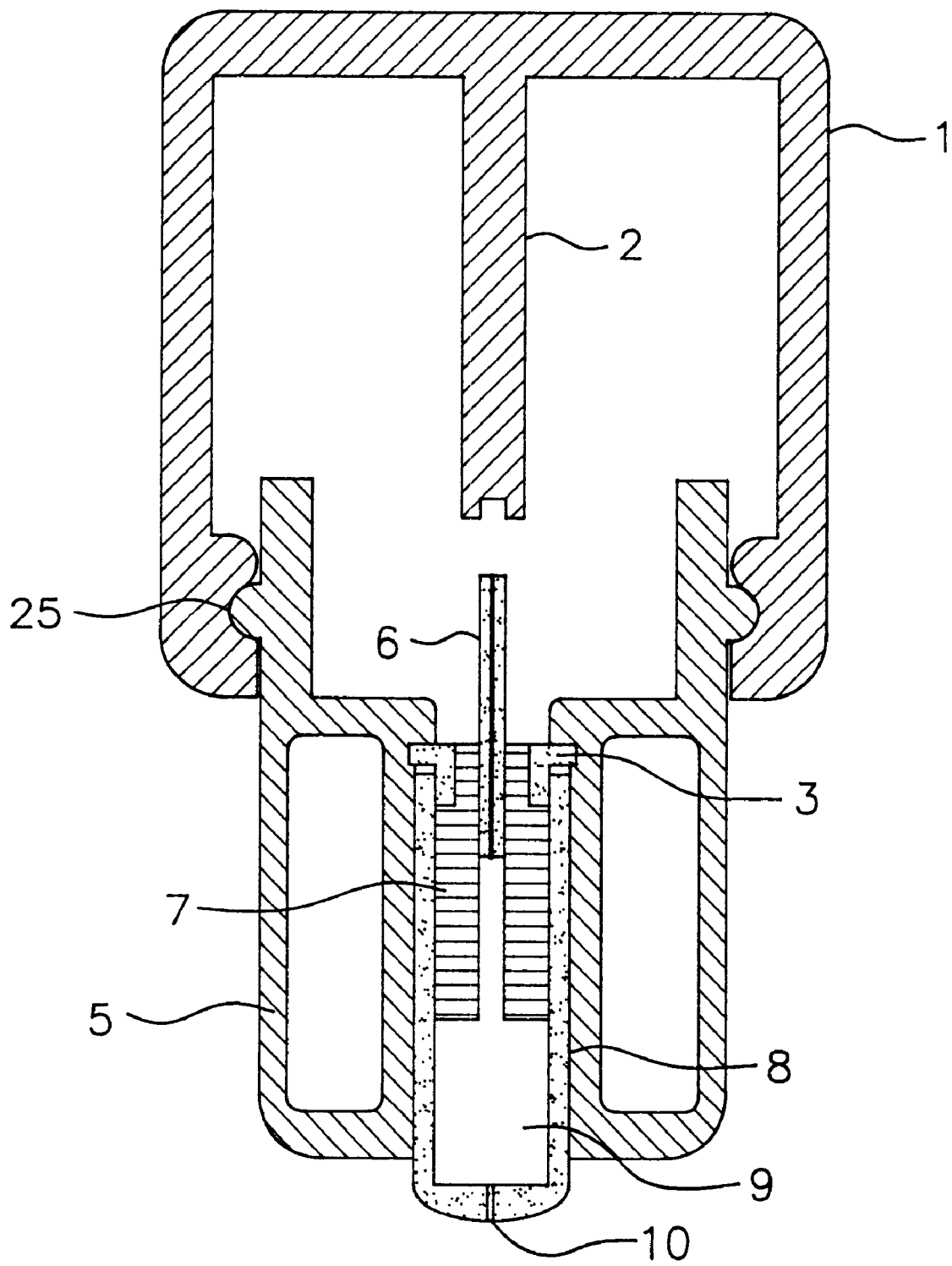
FIG. 9 is a cross-sectional view of a fifth embodiment which is a re-usable jet injector power device where break tabs are replaced with snap rings enabling the power case to be re-used by replacing the injection capsule after re-cocking the power case and drawing the cap back over the base until the snap rings re-engage.

FIG. 9 depicts a re-usable jet injector power case. It is quite simple to convert to the re-usable power case by redesigning the snap component. Snap rings 25 replace the break tabs enabling the power case to be re-used by replacing the injection capsule after re-cocking the power case by drawing the cap 1 back over the base 5 until the snap rings 25 re-engage.

Although specific embodiments of the invention are herein disclosed for purposes of explanation, various modifications thereof, after study of this specification, will be apparent to those skilled in the art to which the invention pertains.

What is claimed is:

1. A hand-operated injector device consisting of a cap, a plunger, a base having a cavity and outer surface, a snap means for resisting movement of the plunger and an injection capsule for injecting by pressurized fluid flow of at least one parenteral medication in the injection capsule through skin of a patient, wherein the improvement comprises:

a central finger centrally located within the cap and being movable relative to the injection capsule;

a narrow plunger centrally located within an annular wide plunger, the narrow plunger being movable separately from and in unison with the annular wide plunger, the narrow plunger and the annular wide plunger forming a composite plunger and forming a part of the injection capsule located within the base; and a dosage capsule having a fine injection orifice at one end and containing liquid medicament also forming a part of the injection capsule;

whereby, the narrow plunger, being suddenly forced downward by the central finger upon breakage of the snap means, generates a high pressure in the injection capsule to force a volume of medicament through the orifice as a high pressure jet to form a track through the skin of the patient.

2. The injector device according to claim 1, wherein the snap means are internally located break tabs which yield to hand pressure.

3. The injector device according to claim 2, wherein the break tabs allow the central finger of the cap to suddenly strike the narrow plunger.

4. The injector device according to claim 3, wherein continued hand pressure drives the narrow plunger through the wide annular plunger so as to punch the track through the epidermis until the central finger of the cap strikes the top of the wide annular plunger.

5. The injector device according to claim 4, wherein the central finger of the cap drives the composite narrow and wide plunger toward the orifice to deliver the bulk of the medicament at a substantially lower pressure through the injection track previously formed by the high pressure jet.

* * * * *